(12) United States Patent
Messer et al.

(10) Patent No.: US 7,784,347 B2
(45) Date of Patent: Aug. 31, 2010

(54) ULTRASOUND PHASED ARRAY DEVICES AND METHODS

(75) Inventors: Barry Messer, Calgary (CA); Jose R. Fuentes, Calgary (CA)

(73) Assignee: Fluor Technologies Corporation, Aliso Viejo, CA (US)

( * ) Notice: Subject to any disclaimer, the term of this patent is extended or adjusted under 35 U.S.C. 154(b) by 0 days.

(21) Appl. No.: 11/814,029

(22) PCT Filed: May 17, 2005

(86) PCT No.: PCT/US2005/017383

§ 371 (c)(1),
(2), (4) Date: Apr. 3, 2008

(87) PCT Pub. No.: WO2005/108973

PCT Pub. Date: Nov. 17, 2005

(65) Prior Publication Data

US 2008/0190205 A1    Aug. 14, 2008

Related U.S. Application Data

(60) Provisional application No. 60/646,038, filed on Jan. 21, 2005.

(51) Int. Cl.
*G01N 29/04* (2006.01)

(52) U.S. Cl. .............................. 73/618; 73/622; 73/629; 73/632

(58) Field of Classification Search ................... 73/618, 73/625, 596, 600, 602, 620, 622, 629, 632
See application file for complete search history.

(56) References Cited

U.S. PATENT DOCUMENTS

| | | | |
|---|---|---|---|
| 4,106,327 A | 8/1978 | Adler et al. | |
| 4,336,958 A * | 6/1982 | Goetzinger | 285/55 |
| 4,406,167 A | 9/1983 | Maeda | |
| 4,435,984 A | 3/1984 | Gruber | |
| 4,522,064 A | 6/1985 | McMillan | |
| 4,558,202 A * | 12/1985 | Bagnall et al. | 219/137 WM |
| 5,060,518 A * | 10/1991 | Aleshin et al. | 73/620 |
| 5,082,160 A | 1/1992 | Leigh | |
| 5,351,655 A | 10/1994 | Nuspl | |
| 5,497,662 A * | 3/1996 | Dykes | 73/634 |
| 5,681,996 A * | 10/1997 | White | 73/622 |
| 5,992,236 A * | 11/1999 | White et al. | 73/622 |
| 6,107,595 A * | 8/2000 | Peterson | 219/118 |
| 6,250,163 B1 * | 6/2001 | MacLauchlan et al. | 73/643 |
| 6,789,427 B2 * | 9/2004 | Batzinger et al. | 73/614 |
| 6,925,882 B1 * | 8/2005 | Fleming et al. | 73/632 |
| 6,948,369 B2 * | 9/2005 | Fleming et al. | 73/588 |
| 7,010,982 B2 * | 3/2006 | Bergman | 73/618 |
| 7,093,490 B2 * | 8/2006 | Kono et al. | 73/602 |
| 7,247,348 B2 * | 7/2007 | Power | 427/249.7 |

OTHER PUBLICATIONS

Progress in the Reliable Inspection of Cast Stainless Steel Reactor Piping Components, 18th International Conference on Structural Mechanics in Reactor Technology (SMIRT 18) bEINING, cHINA Aug. 7-12, 2005.*

* cited by examiner

*Primary Examiner*—J M Saint Surin
(74) *Attorney, Agent, or Firm*—Fish & Associates, PC

(57) ABSTRACT

Contemplated configurations and methods are directed to non-destructive ultrasound testing of stainless steel materials, and especially materials in a difficult-to-reach position, in which a phased array probe is operated using longitudinal waves, wherein the probe is further operated at an angle that provides substantially complete ultrasound coverage when the beam angle is modified.

16 Claims, 3 Drawing Sheets

ULTRASOUND PHASED ARRAY DEVICES AND METHODS

This application claims priority to provisional patent application having Ser. No. 60/646,038, which was filed Jan. 21, 2005, and which is incorporated by reference herein.

FIELD OF THE INVENTION

The field of the invention is ultrasound testing, and especially as it relates to testing of difficult-to-reach welds in stainless steel.

BACKGROUND OF THE INVENTION

Stainless steel weld areas are typically difficult to inspect using ultrasound testing (UT) as relatively large anisotropic grains typically found in austenitic weld metals often distort and/or scatter the ultrasound beam. Most commonly, such deleterious effects are a combination of mode conversion and beam attenuation that is produced by variations in sound velocities amongst the grains with differing orientations and positions.

Mode conversion is an effect that is common in UT and often occurs when the ultrasonic beam strikes an interface between two materials with differing acoustic velocities at an oblique angle. When the beam impinges on the interface the beam is split into reflected and refracted beams having different modes and wave classifications (e.g., longitudinal, transverse, and surface waves). Mode conversions typically split the incident beam, reducing its strength, and produces undesired reflections that can create erroneous indications.

Furthermore, the anisotropic characteristics of stainless steels that produce mode conversion can also contribute to beam distortion, causing attenuation and scattering of the ultrasonic beam as it moves through the material. Attenuation generally refers to the absorption of the sound energy as it passes through the material to thereby generate heat. When the sound is absorbed, the signal-to-noise ratio is reduced making it difficult to distinguish the signal from the background noise. Signal scattering is the deflection of small amounts of acoustic energy out of the main ultrasonic beam. The deflection is the result of interactions between the sound beam and discontinuities in the material such as grain boundaries, inclusions, and defects (scattering is highly dependent on the relation between grain size and ultrasonic wavelength). Both attenuation and beam scattering are well recognized problems when using UT to inspect stainless steel weld areas.

At least some of the effects of mode conversion and beam distortion can be addressed and minimized by using suitable probes and analysis techniques. For example, it is known to reduce undesirable effects of attenuation by using lower frequency probes. However, use of lower frequency typically results in reduced sensitivity and resolution. Low signal-to-noise ratios due to scattering can be alleviated by using focusing probes. Unfortunately, where focused beams are used with standard twin crystal probes, inspection time will drastically increase as such processes often require numerous probes of differing angles and focal points.

Therefore, while some of the difficulties associated with UT of stainless steel may be overcome to at least some degree, all or almost all of such improvements require highly skilled technicians and/or significantly increased UT time. Thus, while numerous UT methods and devices are known in the art, all or almost all of them suffer from one or more disadvantages. Thus, there is still a need to provide improved ultrasound testing devices and methods.

SUMMARY OF THE INVENTION

The present invention is directed to configurations and methods for ultrasound testing in which a phased array probe is used at a probe angle that is sufficient to allow substantially complete ultrasonic inspection of difficult-to-reach areas by variation of the beam angle while using longitudinal waves.

Therefore, in one aspect of the inventive subject matter, a method of testing a stainless steel material has one step in which an ultrasonic phased array probe is provided, wherein the probe is operated such that a beam angle is varied, and wherein the probe is further operated in longitudinal wave mode. In another step, the probe is placed onto a surface of a stainless steel material to be tested at an angle such that by variation of the beam angle in longitudinal wave mode substantially all of the material below the surface can be scanned.

In another aspect of the inventive subject matter, a method of instructing a person to detect a potential flaw in a weld of a stainless steel material includes a step in which information is provided to use an ultrasonic phased array probe, wherein the probe is configured and operated such that a beam angle can be varied. In another step, information is provided to operate the probe in longitudinal wave mode. In yet another step, information is provided to place the probe onto a surface of a stainless steel material at an angle such that by variation of the beam angle in longitudinal wave mode substantially all of the material below the surface can be scanned, and in a still further step, information is provided to operate the probe to thereby scan for a potential flaw in the stainless steel material.

Most preferably, the beam angle is varied between 20 degrees and 70 degrees, while the probe angle is between 60 degrees and 80 degrees. Typically, the tested material below the surface comprises a branch connection fitting (e.g., between a beveled outlet connection and a static casting header and/or modified tee), and/or a full penetration groove weld, which may further include a fillet reinforcement. Among other materials, contemplated materials include those suitable for high-pressure applications (i.e., at least 100 psia), and/or high-temperature operation (i.e., above 300° C.). Most commonly, such materials include various stainless steels and other alloyed metals.

Thus, flaws detectable with contemplated methods especially include cracks, lack of fusion, incomplete penetration, undercutting, surface porosity, and exposed slag inclusions in materials (and particularly welds) for industrial use, including pipelines, boilers, etc., wherein the flaw may be detected at depths of up to, and at least 25 millimeter, and more typically up to and at least 30 millimeter.

Various objects, features, aspects and advantages of the present invention will become more apparent from the following detailed description of preferred embodiments of the invention.

DETAILED DESCRIPTION

The inventors discovered that UT could be significantly improved by using a phased array probe in which a plurality of transmitter elements are coordinately controlled to allow for a predetermined position of a focal point and/or position. Most preferably, the phased array probe is operated using longitudinal waves and has a probe angle relative to the surface that that allows a substantially complete sweep of the ultrasonic beam throughout the material that is to be tested. Most typically, the phased array probe is therefore operated such that the beam angle can be varied substantially.

Figure 1:
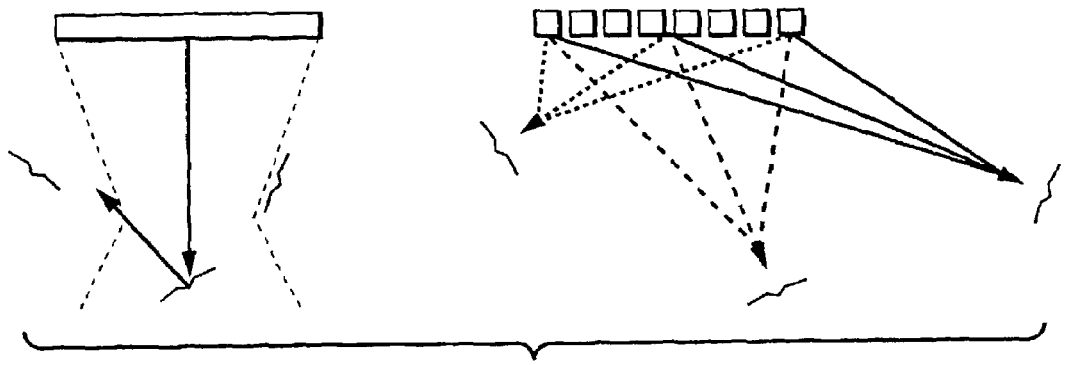
FIG. 1 is a schematic depicting ultrasound wave paths and angles of a probe with monocrystalline transducer (left) and a probe with phased array transducers (right).

An exemplary comparison between a heretofore known ultrasound probe having a single transmitter element is depicted in FIG. 1. On the left side, a monocrystal and on the right side a multi-element probe is shown. The monocrystal probe has a fixed focal point and is limited to defecting flaws with orientations that provide a sufficient back reflection. In contrast, the multi-element probes contemplated herein are able to adjust their focal point and to steer the ultrasonic beam to detect and size cracks of most orientations and depths. As the individual elements are operated in controlled phase relative to each other, testing with contemplated probes and methods is also referred to a UT-PA (Phased Array Ultrasound Testing). Viewed from another perspective, the UT-PA technique is based on an arrangement of multiple piezoelectric elements that are independently controlled for developing synchronized and manageable sonic waves.

Figure 2:
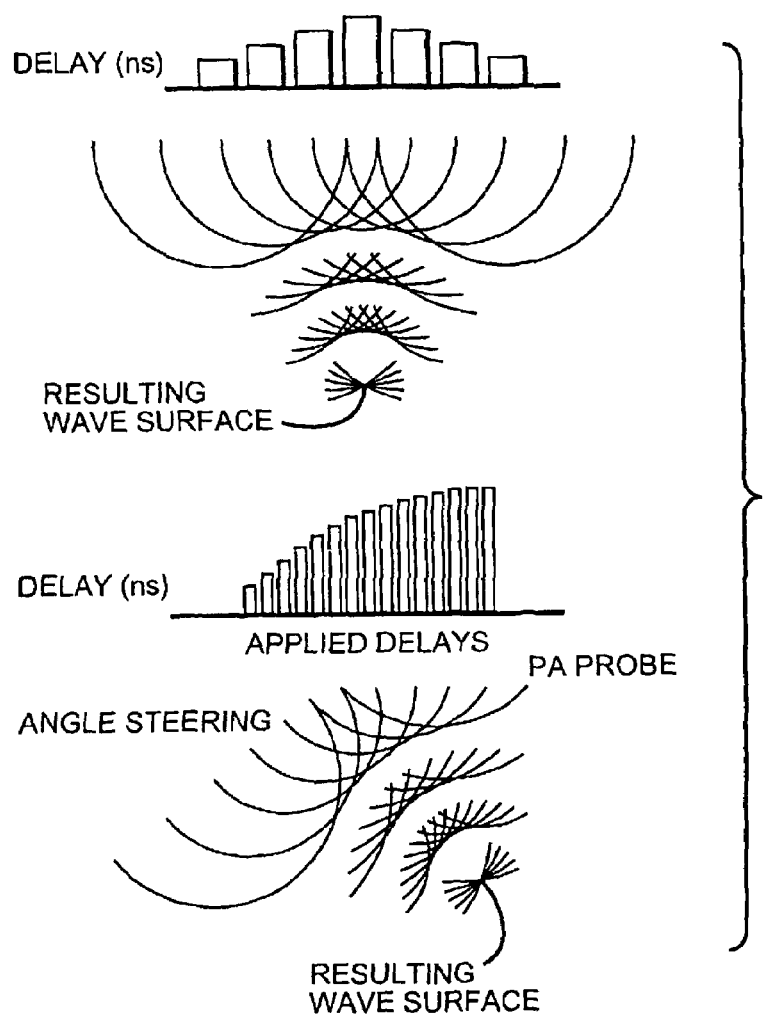
FIG. 2 is a schematic depicting the effect of delayed actuation of transducers in a phased array on beam angle and focal depth.

FIG. 2 depicts exemplary resulting waveforms and directions as a result of controlled delay between the individual elements. In the above panel, the delay of operation of the elements increases from the outside elements to the center elements resulting in a focused beam, while in the lower panel the delay increases in a non-linear fashion from the elements on the left to the elements on the right, resulting in an angled beam. It should be recognized that the so expanded capabilities of UT-PA provides higher resolution with better sizing and mapping characteristics, which can be performed in a fraction of the time required when using conventional UT methods. Moreover, it should also be appreciated that contemplated techniques allows verification of weld integrity for difficult to access welds, including branch connection fittings and full penetration groove welds with fillet reinforcements. Verification of these types of welds is a necessity for power, oil and gas facilities, in particular, those operating under high pressure, temperature, and corrosive environments.

Historically, visual inspections of welds and radiograph testing (RT) have been used, but these methods are costly, time-consuming, and can often not match the benefits of the new UT-PA method. UT-PA methods contemplated herein generally require less time than conventional UT, are not as hazardous as RT, and allow for 100% volumetric inspection. Other advantages of UT-PA contemplated herein include its ease of use, increased accuracy, and development of instantaneous digital inspection records for tracking defect propagations in the future.

The inventors found that, next to other materials, phased array ultrasonics presented a suitable technique for the inspection of cast stainless steels, and particularly ASTM A608 modified 20Cr-32Ni—Nb stainless steel. Using contemplated methods and devices, weld integrity for difficult to access areas such a branch connection fittings and groove welds can now be tested in a non-destructive manner. This safe, easy-to-use, and efficient technique can be applied to 100% of the weld volume and offers a weld and check method with instantaneous digital results. The present UT-PA method also provides a simple cost efficient method of focusing on potential problem areas and thus, reduces the need for costly repairs. In contrast, most conventional UT cannot be successfully implemented in all of the difficult to access areas. Other methods of non-destructive testing of difficult to access areas required visual checks or relatively expensive examination methods that subject the users to various hazards (e.g., radiation, chemicals, etc.).

A comparison of UT-PA methods contemplated herein with other testing methods is shown in Table 1 below in which UT-TOFD refers to ultrasonic testing with time-of-flight detection. The probability of detection (POD) results are from a survey of the Dutch welding institute.

| CHARACTERISTIC | RT | Conventional UT | UT-TOFD | UT-PA |
|---|---|---|---|---|
| Sizing capabilities | Detection yes, no vertical sizing | Detection yes, limited vertical sizing | Very good, detection and sizing | Very good, detection and sizing |
| Coverage | Full | Full | Some limitations, at the ID/OD surfaces | Full |
| Reproducibility | Good | May vary with operator | Good | Good |
| Defect type, orientation limitations | Good for volumetric defects, limited for planar defects | Good for planar defects, somewhat limited for volumetric defects | Good for planar and volumetric defects | Good for planar defects, somewhat limited for volumetric defects |
| Material limitations | Limited to thickness less than 2" (Ir. 192) | Limited on austenitic materials | Less suitable for coarse grained materials and clad, no thickness limitation | Generally no limitations |
| Data presentation | Top view | None | Side view | Top-side-end view |
| Geometric considerations | Generally limited to butt welds, for piping and vessels | Generally, no limitations | Generally limited to butt welds, for piping and vessels | Can be adopted to fit geometric conditions |
| POD | 66% | 52% | 82% | 89% |
| Operator experience | Qualified technicians | Qualified technicians | Well trained operators are essential | Well trained operators are essential |

-continued

| CHARACTERISTIC | RT | Conventional UT | UT-TOFD | UT-PA |
|---|---|---|---|---|
| Operator dependence | Yes, to some degree during interpretation | Yes, based on experience | Not so much, due to digital archiving | Not so much, due to digital archiving |

EXAMPLES

Figure 3:
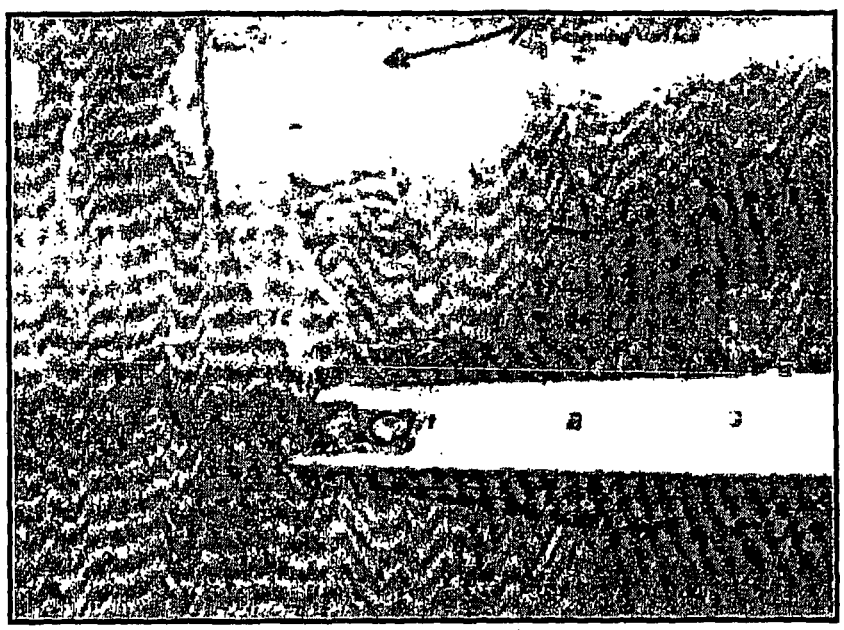
FIG. 3 is a photograph of an exemplary welded connection depicting the scanning surface.

The examples below describe various aspects of non-destructive UT-PA techniques according to the inventive subject matter on a branched connection of an ASTM B564 outlet fitting to both an ASTM A608 modified 20Cr32Ni—Nb static casting header and an HP45 modified tee. In the examples, accurate and fast verification results for the reinforced fittings were obtained. An typical single welded connection is shown in FIG. 3, which is representative of branch connections to be inspected using UT-PA.

The fittings of the equipment and materials under inspection included (1) UNS N08811 ASTM B564 MSS SP-97-2001 outlet fittings with bevel design and dimensions, according to ASME B 16.25, ID=28.5 mm and Max OD=89.5 mm, average wall thickness t=30.5 mm, (2) ASTM A608 modified 20Cr-32 Ni—Nb pipe headers with an ID=279.4 mm and wall thickness t=38.1 mm, and (3) HP45 modified tees.

Considerable challenges are often encountered on a construction site in examining weld integrity for the branch connections as welds may be in locations where pipe wall configurations makes examination by traditional RT methods very difficult and time consuming. In addition, and especially where sample radiograph tests provide poor results, alternative examination methods become highly desirable. The Code defines branch connections as "an integrally reinforced fitting welded to a run pipe and connected to a branch pipe by butt welding, socket welding, threaded, or flanged joint, including a branch outlet fitting conforming to MSS SP-97". For RT examination, this means that acceptance criteria for the welds are not allowed to have any cracks, lack of fusion, incomplete penetration, undercutting, surface porosity, or exposed slag inclusions.

During RT sample trials, a total of 25 outlet fittings were tested with double wall exposure technique. Six (24%) were rejected as per B31.3 Table 341.3.2 category M fluid under the column "girth, miter groove and branch connection". Challenges associated with doing this type of double wall exposure were related to the extensive time and effort involved (about 6 hours to examine a complete connection). For example, with over 600 branch connections to be inspected, RT methods would have required more than five months to complete with crews working non-stop. The new phased array technique presented herein proved to be a highly desirable alternative by accomplishing the inspection in ten working days. Another RT examination employed the single wall exposure technique. This technique was permissible at certain locations due to the connection configuration and pipe wall size. Results of these examinations showed a total of 29 rejected connections out of 45 inspected for a 64.4% rejection rate for the samples. The "geometric unsharpness" factor for these welds, however, was not in compliance with Section V Article 2 paragraph T-274.2 for material thickness less than 2".

There were two main issues to consider for use of UT-PA. One was the compliance of the UT-PA technique to Code, and the other was its applicability for use with tools currently available for the welding configurations. The design conditions involved pressures at 485 psig and temperatures at 1625° F. (885° C.). Design was based on API 560 Fired Heaters for General Refinery Service and ASME B31.3 Process Piping. Acceptance criteria for these welds using RT fell under ASME Code B31.3, Table 341.3.2. The ASME VIII Pressure Vessel Code, case 2235-6 allowed "Use of UT in lieu of RT", and the statements of API-560 and B31.3 supported UT examination. The API-560 Code, paragraph 14.2.2.7 states "In cases where weld or material configuration makes radiographic examination difficult to interpret or impossible to perform, such as nozzles welds, ultrasonic examination may be substituted". Further, the ASME B31.3 Code, paragraph 341.5.3, Examinations to Resolve Uncertainty, states "any method may be used to resolve doubtful indications".

Calibration

Figure 5:
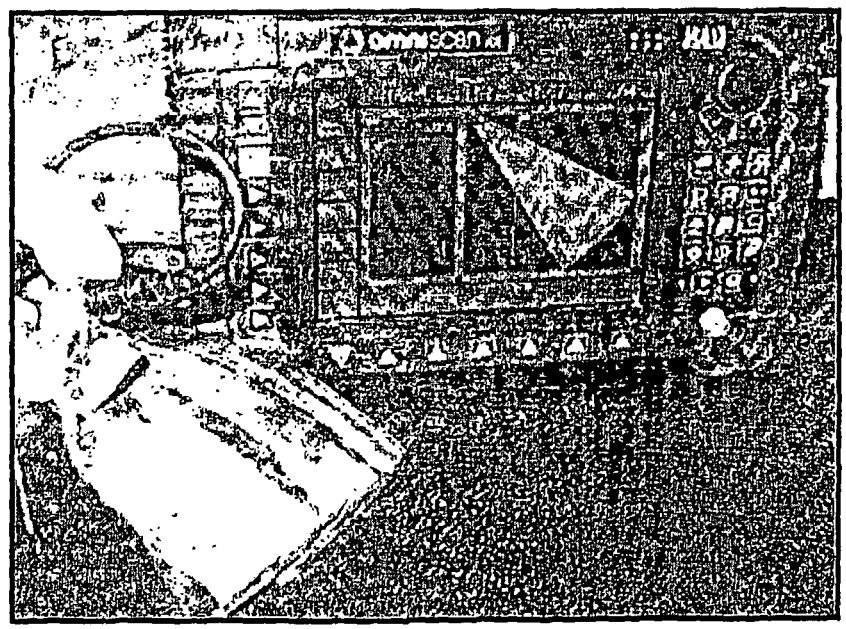
FIG. 5 is a photograph of an exemplary configuration according to the inventive subject matter.
Figure 4:
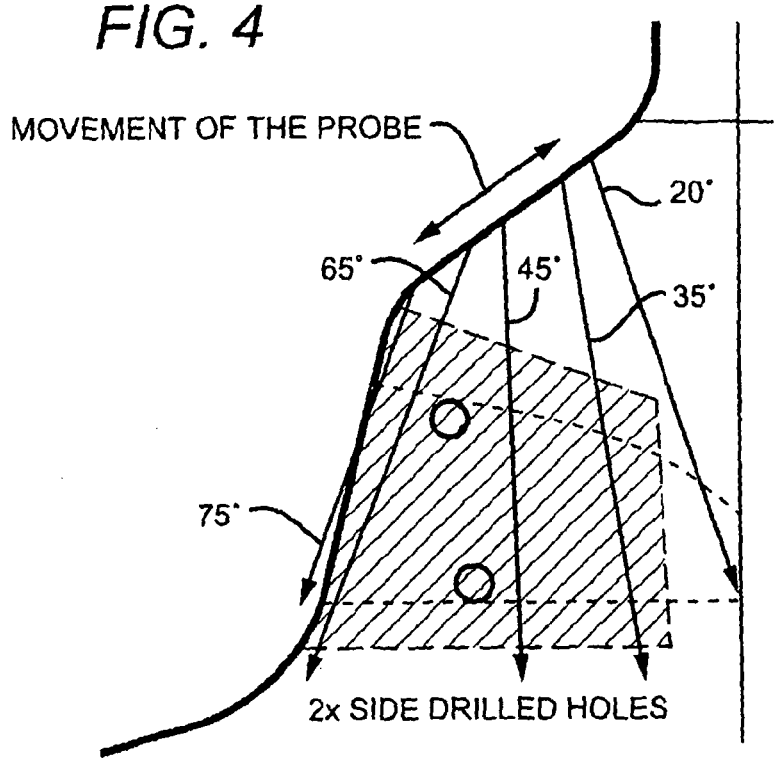
FIG. 4 is a schematic cross section of the welded connection of FIG. 3.
Figure 6:
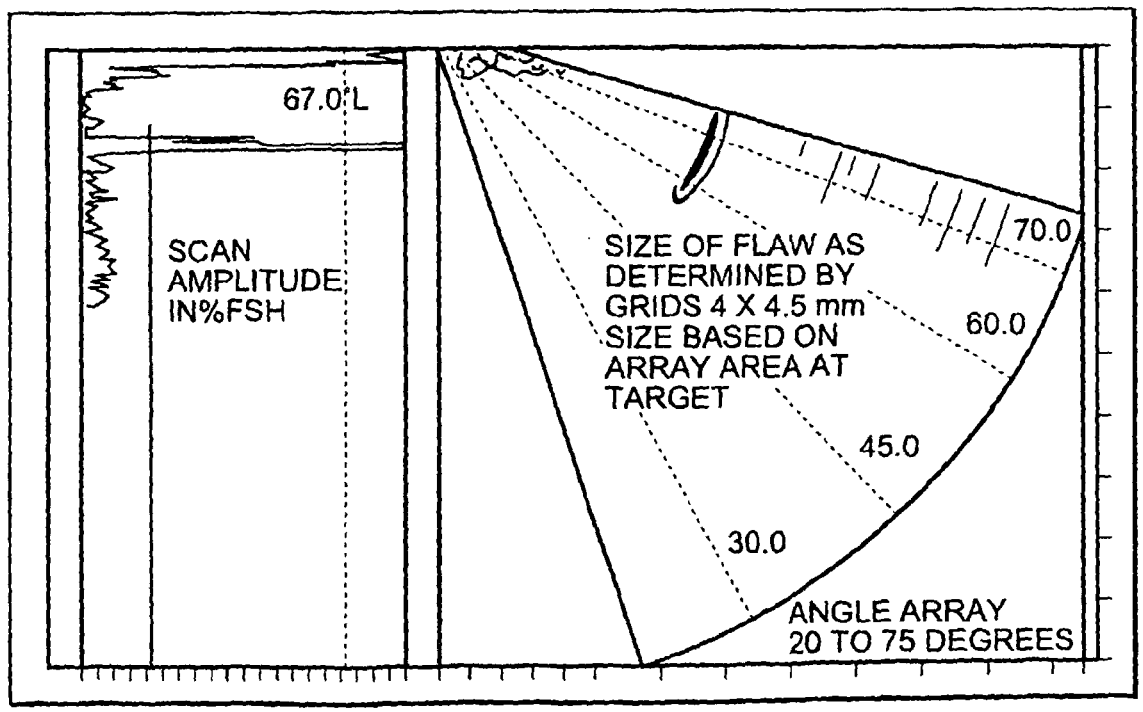
FIG. 6 is an exemplary screen output of a scan in which the beam angle is varied between 20 and 75 degrees.

To calibrate the UT-PA device, actual outlet fitting samples were taken and used as "calibration blocks". FIG. 4 illustrates the use of these samples for calibration. The calibration piece with side-drilled holes was prepared from a welded branch to tee connection sample. This sample is representative of all the connections examined, in terms of weld preparation, process and heat treatments. As shown in FIG. 5, an R/D TechOmniscan instrument was used with a 16-element probe at 5.0 MHz and ultra gel couplant suitable for most stainless steel applications. The UT-PA technique is suitable with a CGSB UT Level II or SNT UT Level II, and only requires two to three days of training before on-screen interpretations of results can be made. A sample output for the technique is shown in FIG. 6.

It should be noted that the selected probe angle should be suitable for the expected defect orientation. Consequently, it is preferred that the incident angle of the ultrasonic beam should strike a defect perpendicular for maximum echo amplitude. However, determining this proper probe angle is difficult when flaw orientation is not known before hand. For this situation, the weld was scanned from the flat surfaces of the outlet fitting. Most generally probe angles employed herein were between 5 degree and 85 degree, more commonly between 25 degree and 80 degree, and most commonly between 60 and 80 degree.

Commonly, only transverse (shear) wavelengths are generally allowed for weld inspection. However, where such parameters are not practicable and/or feasible, it should be recognized that longitudinal (straight) wavelengths can be used such that the required sectional scan width can be achieved. Shear waves have about half the wavelength of longitudinal waves and can only be spread open to a 30 to 35 degree coverage angle. In contrast, longitudinal waves can be widened twice as much as illustrated in FIG. 4 (Sample connection used as a "calibration block" for the UT-PA equipment). Therefore, it should be recognized that by using longitudinal waves, sectorial coverage of 10 degrees to 80 degrees, and more typically 20 degrees to 75 degrees can be achieved. In combination with the appropriate probe angle, substantially complete coverage of the scanned area can be achieved. The terms "substantially complete" and "substantially all" as used herein refers to at least 90%, and more typically at least 95%, and most typically at least 97%-100%. The scan was programmed in 1-degree increments of the ultrasonic beam and had an angular resolution of 0.8 mm.

The grains of the weld material were determined to be an average size of 8 based on ASTM E-112-96 Table 4 (the pieces were cut perpendicular to the weld axis to show the structure and the weld fusion faces). The holes were respectively drilled at the fusion zones. The purpose of calibrating through the fusion zone and weld material was to compensate for the effects of the weld structure. FIG. 6 depicts a screen view that is taken from the location on a connection where the maximum amplitude was detected, showing the coverage of the array, which for this application is from 20 to 75 degrees. It also displays the angle at which maximum energy was reflected from the indication, 67 degrees longitudinal wave. The screen depth scale cannot be used to determine flaw depth as the taper affects distance, depending on the location of the probe on the welded connection. As well, the velocity changes in the weld material can make this less accurate. However an estimated distance from the OD surface is given in the results tables, which is based on where the indication appears within the array. Based on the relatively short sound paths of the reported indications, it is believed that they are positioned at the weld zone on the welded side of the connection. Defect sizes are estimated based on the cross section of the array (approximately 10 to 12 mm) at the target. The estimated sizes are directly and proportional taken from the images.

The sensitivity is mainly determined by the size of the side-drilled holes, which were 1/8" (3.2 mm.) in diameter in accordance with B31.3 requirements for a weld thickness of 30.5 mm. Sensitivity calibration was carried out on the 1/8" diameter holes, scanning with an extra 6 dB of sensitivity in order to size the indications. For evaluation of indications and data collection, the extra 6 dB was removed.

Correlation of UT-PA Versus RT

According to the ultrasonic acceptance criteria of the ASME B31.3 Code, paragraph 344.6.2, a linear-type discontinuity is unacceptable if the amplitude of the indication exceeds the reference level and its length exceeds 10.2 mm. This equals to a 10 mm length for field applications where there is a 0.2 mm measurement uncertainty. As a result, indications had to exceed two criteria. First, the flaw must be displayed 80% or more over the full screen height and second, the flaw must be 10 mm or longer to be considered a reject.

The 10.2 mm length comes from the letter "F"=T/3 where T is the nominal wall thickness of the thinnest component joined by the weld. For linear-type discontinuities, if the amplitude of the indication exceeds the reference level and its length exceeds T/3 for thickness between 19 to 57 mm (actual thickness considered was 30.5 mm), the sample will be considered a reject (Should ASME Section VIII Division I have been taken as the main code for the acceptance criteria, then the criteria would have been the same as ASME B31.3).

A trial of correlation RT versus UT-PA was established in a sample of 25 branched connections. This resulted in a 100% correlation of signal or, in some cases, an indication providing evidence that UT-PA located more flaws than RT. When a strict code criterion was applied to these 25 connections, UT-PA rejected 8% more than RT (28% for UT-PA in comparison to 20% for RT). It should be noted that UT-PA rejection was based on flaw length, as specified by B31.3 paragraph 344.6.2; whereas RT rejection was based on defect length and width, as indicated by B31.3 Table 344.3.2. Therefore, a decision was made to continue testing all the other welds with the UT-PA method. Data samples of the correlations tests for the UT-PA and RT methods are shown in FIG. 9 and FIG. 11.

Analysis of the correlation of UT-PA to RT provided evidence of the efficiency and accuracy of UT-PA based on location and sizing of flaws. Table 2 summarizes the properties for both of the testing methods used.

| Characteristic | RT Single-wall | RT Double-wall | UT-PA |
|---|---|---|---|
| Time spent to test a single connection | 1 Hr | 6 Hr | 10 min |
| Total time required for all connections | N/A, since it did not complied with code | 5 months | 10 days (actual time spent) |
| Time to get results | Day after (or minimum developing time) | Day after (or minimum developing time) | Immediate |
| Impact to work surrounding test area | Total isolation due to radiation hazard during shooting | Total isolation due to radiation hazard during shooting | None |
| Code compliant | No | Yes | Yes |
| Cost | At least four times the cost of UT | At least four times the cost of UT | At least 1/4 the cost of RT |
| Coverage and resolution | Unable to see root portion of the weld | Difficult to interpret | 100% clear volumetric coverage |
| Flaws identification | Yes, but to the root portion | Yes | 1 to 1 compared to RT |
| Proof of test | RT film + NDE Level III Report | RT film + NDE Level III Report | CD with color images + NDE Level III Report |

UT-PA Results

The UT-PA method presented herein indicated a 20.5% rejection rate with a total of over 100 connections failing to meet acceptance criteria of the more than 600 tested. There were about 100 outlet fittings on branches and about 30 fittings on tee locations.

In addition to the tested and identified connections with defects warranting rejection, a complete scan was requested and performed on all connections with any indications. Only rejected connections were repaired or replaced. There were a total of 442 connections with lengths under 10 mm that were not rejected. These identified indications will be monitored in the future using the same UT-PA technique. At that time, the future ultrasonic results will be crosschecked with the records obtained during this UT-PA examination. Therefore, behavior or propagation of defects can be identified and actions taken accordingly for repair or replacement.

Consequently, it should be recognized that numerous advantages and benefits are achieved using the UT-PA method as presented herein. Among other things, UT-PA technology allows for electronic beam steerage and focus to cover the weld area from a limited scanning surface, such as the 45° degree tapered area of a reinforced branched connection. Moreover, contemplated technology provides 100% volumetric assessment, and the digital results provide cross sectional images of indications and permanent records of collected data. Still further, UT-PA gives faster results in comparison with RT, which typically requires considerable developing and exposure times, especially for thick walls. Moreover, the UT-PA achieves good testing results in most metallic welds and metallic materials, is easy to use, and non-hazardous to persons conducting the tests.

It should be especially appreciated that the complex welds analyzed above included heavy wall butt welds and reinforced fitting to header welds comprising HP45 modified metal with a precipitation hardened static high alloy casting, which were relatively difficult to examine (in some cases, the probe angle needed to be modified to about 70 degrees, and the waveform was changed to a longitudinal wave to obtain coverage and energy required to get both the root and the fill). Thus, and particularly on the basis of the excellent results from heavy and thin wall HP45, it should be recognized that UT-PA is also deemed suitable for numerous other metals and metal alloys, and especially for carbon steel, low alloy, and stainless steel. Furthermore, among various other uses for contemplated materials, UT-PA is thought to be particularly advantageous for examination of stub in, stub on, and outlet type attachment welds to pressure vessels and equipment.

Thus, it should be recognized that UT-PA is a reliable method of examination where RT cannot be used. For example, the new UT-PA technique provides more detailed results with excellent presentation of records that are easy to read and support future preventative maintenance. Furthermore, there are minimal costs associated with training and interpreting results, and code compliance can be achieved with greater certainty than with other RT methods.

Consequently, the inventors contemplate a method of testing a stainless steel material has one step in which an ultrasonic phased array probe is provided, wherein the probe is operated such that a beam angle is varied, and wherein the probe is further operated in longitudinal wave mode. In another step, the probe is placed onto a surface of a stainless steel material to be tested at an angle such that by variation of the beam angle in longitudinal wave mode substantially all of the material below the surface can be scanned. Viewed from another perspective, the inventors contemplate a method of instructing a person to detect a potential flaw in a weld of a stainless steel material includes a sep in which information is provided to use an ultrasonic phased array probe, wherein the probe is configured and operated such that a beam angle can be varied. In another step, information is provided to operate the probe in longitudinal wave mode. In yet another step, information is provided to place the probe onto a surface of a stainless steel material at an angle such that by variation of the beam angle in longitudinal wave mode substantially all of the material below the surface can be scanned, and in a still further step, information is provided to operate the probe to thereby scan for a potential flaw in the stainless steel material Thus, specific embodiments and applications of non-destructive phased array ultrasound testing of stainless steel materials have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A method of testing weld integrity of a weld in a stainless steel material, comprising:
   providing an ultrasonic phased array probe, wherein the probe is operated such that a beam angle is varied, and wherein the probe is operated in longitudinal wave mode;
   placing the probe onto a surface of a stainless steel material to be tested at an angle such that by variation of the beam angle in longitudinal wave mode substantially all of the material below the surface is scanned; and
   operating the probe to allow scanning for a potential flaw in the stainless steel material, such that the flaw is detectable at a depth of at least 25 mm.

2. The method of claim 1 wherein the beam angle is varied between 20 degrees and 70 degrees.

3. The method of claim 1 wherein the probe angle is between 60 degrees and 80 degrees.

4. The method of claim 1 wherein the material below the surface comprises at least one of a branch connection fitting, and a full penetration groove weld, optionally with fillet reinforcement.

5. The method of claim 4 wherein the branch connection fitting is between a beveled outlet fitting and at least one of a static casting header and a modified tee.

6. The method of claim 1 wherein the flaw is selected from the group consisting of a crack, a lack of fusion, an incomplete penetration, an undercutting, a surface porosity, and an exposed slag inclusion.

7. The method of claim 1 wherein the material below the surface has a thickness of at least 30 millimeter.

8. The method of claim 1 wherein the material below the surface comprises stainless steel suitable for high-pressure operation.

9. A method of instructing a person to detect a potential flaw in a weld of a stainless steel material, comprising:
   providing an information to use an ultrasonic phased array probe to test weld integrity of a weld in a stainless steel material, wherein the probe is configured and operated such that a beam angle is varied;
   providing information to operate the probe in longitudinal wave mode;
   providing information to place the probe onto a surface of a stainless steel material at an angle such that by variation of the beam angle in longitudinal wave mode substantially all of the material below the surface is scanned; and providing information to allow scanning for a potential flaw in the stainless steel material, such that the flaw is detectable at a depth of at least 25 mm.

10. The method of claim 9 wherein the beam angle is varied between 20 degrees and 70 degrees.

11. The method of claim 9 wherein the probe angle is between 60 degrees and 80 degrees.

12. The method of claim 9 wherein the material below the surface comprises at least one of a branch connection fitting, and a full penetration groove weld, optionally with fillet reinforcement.

13. The method of claim 12 wherein the branch connection fitting is between a beveled outlet fitting and at least one of a static casting header and a modified tee.

14. The method of claim 9 wherein the flaw is selected from the group consisting of a crack, a lack of fusion, an incomplete penetration, an undercutting, a surface porosity, and an exposed slag inclusion.

15. The method of claim 9 wherein the material below the surface has a thickness of at least 30 millimeter.

16. The method of claim 9 wherein the material below the surface comprises stainless steel suitable for high-pressure operation.

* * * * *